United States Patent
Stedman

[11] Patent Number: 6,063,110
[45] Date of Patent: May 16, 2000

[54] MEDICAL DEVICE

[76] Inventor: Veronica Mercia Stedman, 10 Fiona Street, Chapel Hill, Queensland, 4069, Australia

[21] Appl. No.: 08/972,956

[22] Filed: Nov. 19, 1997

[51] Int. Cl.[7] ................................................. A61F 07/00
[52] U.S. Cl. .......................... 607/108; 607/112; 607/114
[58] Field of Search ............................ 607/96, 108–112, 607/114

[56] References Cited

U.S. PATENT DOCUMENTS

| | | | |
|---|---|---|---|
| 5,050,595 | 9/1991 | Krafft . | |
| 5,133,348 | 7/1992 | Mayn | 607/108 |
| 5,235,974 | 8/1993 | Miller . | |
| 5,304,215 | 4/1994 | MacWhinnie et al. | 607/108 |
| 5,441,534 | 8/1995 | MacWhinnie et al. | 607/108 |
| 5,476,490 | 12/1995 | Silver | 607/108 |
| 5,507,794 | 4/1996 | Allen | 607/114 |
| 5,679,052 | 10/1997 | Rucki | 450/57 |
| 5,776,177 | 7/1998 | MacWhinnie et al. | 607/108 |

FOREIGN PATENT DOCUMENTS

| | | |
|---|---|---|
| 891872 | 2/1981 | Belgium . |
| 8604038 | 8/1986 | Brazil . |
| 2848088 | 5/1980 | Germany . |
| 3617703 | 12/1986 | Germany . |
| 217543 | of 0000 | New Zealand . |
| 178050 | 2/1957 | New Zealand . |
| 113802 | 12/1976 | New Zealand . |

*Primary Examiner*—Robert L. Nasser
*Attorney, Agent, or Firm*—Delio & Peterson, LLC

[57] ABSTRACT

The present invention relates to a device for the relief or treatment of painful or tender breasts in a lactating women comprising, a support attachable to a womens upper body and a breast cover mounted to said support for at least partially covering one or both breasts, whereby in use said breast cover induces localised heating or cooling in at least part of said one or both breasts.

6 Claims, 1 Drawing Sheet

MEDICAL DEVICE

BACKGROUND OF THE INVENTION

The present invention relates to a device for the relief and/or treatment of sore and tender breasts in lactating women.

Many women when breast-feeding infants suffer from sore and tender breasts. This is often painful and extremely uncomfortable. Some relief is generally obtained by having a warm shower or bath. This is clearly not always convenient, especially if away from the home. Hot and cold packs or wraps are known for use in the treatment of injured joints. Such cold and hot packs may be placed on the breasts. However, such packs are intended for treatment of an immobilised limb. Use of such packs by a lactating woman requires the woman to remove at least part of her clothing. This is often inconvenient and embarrassing. Further, she must lie down or hold the packs to keep them in place.

It is not practically possible for a woman to employ any of the above methods for obtaining relief for extended periods of time, nor is it possible for the woman to employ these methods in public.

SUMMARY OF THE INVENTION

It is an object of the present invention to provide a device which may overcome the above disadvantages and provide the public with a useful choice.

According to a first embodiment of the present invention there is provided a device for the relief or treatment of painful or tender breasts in a lactating woman comprising:

a support attachable to a woman's upper body;

a breast cover comprising a water absorbent material and which is mounted to said support for at least partially covering one or both breasts, whereby in use said breast cover can induce either localised heating or cooling in at least part of said one or both breasts.

According to a second embodiment of the present invention there is provided a method for the relief or treatment of painful or tender breasts in a lactating woman which method comprises the steps of heating or cooling the breast cover as defined in the first embodiment, mounting the cover to said support and attaching said support to a woman's upper body such that said cover at least partially contacts one or both breasts.

The device and method may be used to treat or relieve most conditions in which a lactating woman experiences sore or tender breasts. Typical conditions include engorged breasts or blocked ducts.

The support may be of any shape or size which may be attached to or worn by a woman. Preferably the support is adjustable to allow it to be worn by women of different sizes. Preferably the support is made from a flexible fabric which may be natural or synthetic. Suitable materials include cotton or nylon. Typically, the support has a similar shape to that of a brassiere.

The breast cover may be a single unit or preferably may be provided in two separate parts, one part for each breast. Preferably, the cover will be shaped to fit comfortably over the breast or breasts. The cover is preferably large enough to cover a sufficient proportion of the or each breast to provide relief. Preferably, the cover will be large enough to completely cover the breast.

The cover may have a centrally located hole to allow the nipple to protrude during use. A cover of this type may be used if heating or cooling of the nipple is not desirable. Alternatively, the cover may extend over the nipple so that it is not exposed. This type of cover may be used in the treatment of other conditions such as cracked nipples which are often experienced by lactating women. Heating or cooling of the nipple may provide some relief for these conditions. Also the cover may be impregnated with a medicament suitable for treatment of such conditions. It can be seen that this offers an easy and convenient method for administering medication to the nipple over a period of time.

The cover may be made from any suitable material capable of inducing localised heating or cooling of body tissue. A suitable material is a hydrogel material which may be readily heated or cooled by known means. For example, the cover may be placed in a freezer or microwave oven. Alternatively, the material from which the cover is made may be a water absorbent fabric. In this case the cover may absorb hot or cold water. Alternatively, the cover may absorb water at room temperature and then be refrigerated or heated prior to use.

In order to minimise or prevent water from the cover being absorbed by the support and in turn wetting the wearer's outer clothing, the support is preferably lined with a water resistant material such as a plastic material. Preferably the material is breathable to minimise condensation. Alternatively the cover may have a water resistant layer on that side which abuts the support.

Preferably the material will not irritate the skin. However, a protective pad may be placed between the breast and the cover to alleviate any discomfort.

Additional, or "spare" covers may be stored in the freezer for immediate use. The covers may be washable and re-useable or may simply be disposed of after use.

The cover may be permanently or detachably mounted to the support. Preferably the cover is detachably mounted for ease of heating and cooling. The cover may be mounted to the support by any suitable means. The support may have a portion having a complimentary shape to the cover and may simply hold the cover in place. Attachments may also be provided to assist in mounting the cover to the support. For example, the cover may be clipped or buttoned or a hook and eye type fastener such as that sold under the trade mark VELCRO may be used.

The present inventor has also found that engorgement of the breast can be controlled and pain or discomfort alleviated if the or each breast is cooled shortly after breast feeding. The or each breast may be kept cool as desired until prior to the next feed. As the temperature of the cooled covers warm with use they can be replaced with cool covers as desired. Prior to feeding the cold covers are preferably replaced by warm covers to stimulate localised warming of the or each breast. After feeding the or each breast is cooled in the manner as described above. In this way the woman may control the engorgement of her breasts in a manner which has not before been possible.

It can be seen that when the device is worn by a wearer, the wearer may move about freely without having to manually hold a flannel in place. Further, clothing may easily be worn over the device and no embarrassment or inconvenience need be suffered.

BRIEF DESCRIPTION OF THE DRAWINGS

By way of example only, reference will now be made to a preferred embodiment of the invention as illustrated in the attached drawing in which.

DESCRIPTION OF THE PREFERRED EMBODIMENT

Figure 1:
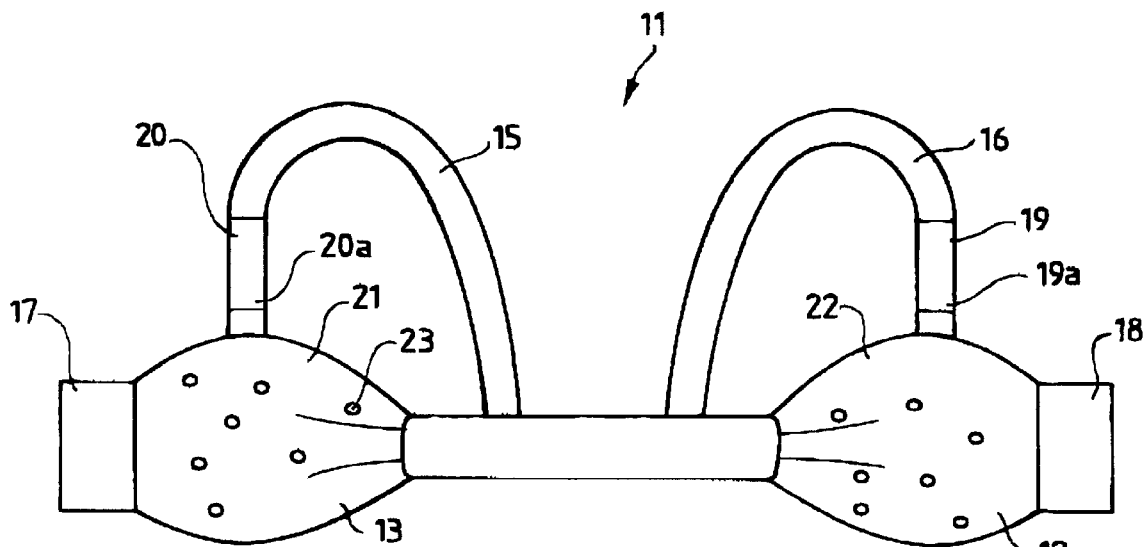
FIG. 1 is a plan view of a support of the present invention.

FIG. 1 illustrates a support 11. The support has two breast supporting portions 12, 13 connected by a bridging portion 14. Two U shaped straps 15, 16 extend between bridging portion 14 to a respective breast covering portion. Each breast supporting portion has a free end to which is sewn complementary hook and eye portions of velcro 17, 18. Further complementary hook and eye portion of velcro tabs 19, 19a, 20, 20a are provided on each U strap. These tabs enable the length of the straps to be adjusted.

The breast supporting portions are made from a cotton fabric material. The inner faces 21, 22 are lined with a water resistant plastic material. This is to minimise passage of water or moisture through the fabric to the outer face. Air holes 23 are provided in the plastic cover to minimise condensation.

Figure 2:
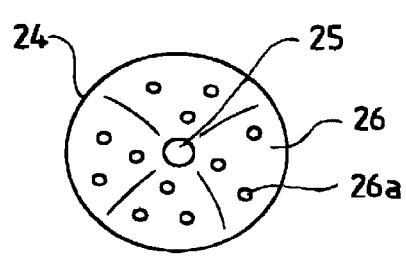
FIG. 2 is a plan view of a cover for use with the support of FIG. 1.

FIG. 2 illustrates a breast cover 24 for use with the support of FIG. 1. The cover 24 has a circular shape and is made from a cotton or like material. One side of the cover has a plastic lining 26. The lining has a number of air holes, 26a. The cover and jacket each have a centrally located opening 25. The holes are large enough to allow the nipple to protrude through the cover and jacket. Thus, the nipple is not subjected to any heating or cooling.

Figure 3:
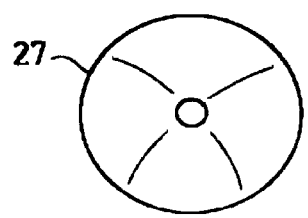
FIG. 3 is a plan view of a protector for use with the cover of FIG. 2.

FIG. 3 illustrates a protector for use with the cover of FIG. 2. The protector 27 is about the same shape as the cover. It is made from paper or similar material and may be disposed of after use. The protector is placed between the breast and the cover. The protector and cover are held in place on the breast by the support 11.

In use the covers are heated or cooled as required. The user places the arms through U straps 15, 16 which will then be positioned over the shoulders such that bridging portion 14 locates across the back and breast covering support 12, 13 locate about the breast. The support 11 is secured by joining velcro tabs 17, 18 between the breasts. It is especially preferred that the support be joined in this way as it allows the covers to be removed and replaced without removing the support. The covers and protectors, if desired, are placed between the breast and support. The cover is placed such that its plastic lining lies adjacent the support. This minimises passage of water adsorbed in the cover from soaking through to the support and hence to the woman's outer garments. It can be seen that when the support is lined with a water resistant plastic material it may not be necessary for the covers to also have a plastic lining. The covers will be held in place on the breast by the support.

It can be seen that normal clothing may be worn over the support and it will not impede or obstruct everyday activities. The device can also be used to heat or cool the device as desired. Still further, the device is breathable and is comfortable to wear for extended periods.

It should be appreciated that various other changes and modifications may be made to the embodiment without departing from the spirit or scope of the invention.

What is claimed is:

1. A device for the relief and treatment of painful or tender breasts in a lactating woman comprising:

a support attachable to a woman's upper body having an inner and an outer surface;

a breast cover for insertion in said support between the inner surface and the breast for at least partially contacting and covering one or both breasts comprising a water absorbent material for at least partially covering and contacting one or both breasts adapted to absorb a sufficient amount of water therein to induce either localized heating or cooling of one or both breasts, and a water resistant lining having a plurality of apertures contacting the inner surface of said support.

2. The device of claim 1 further including a second breast cover such that each cover conforms to each breast of a woman.

3. The device of claim 1 wherein said water resistant lining is air permeable.

4. The device of claim 1 further including a removable protector adapted to be placed between said breast cover and one or both breasts.

5. The device of claim 1 wherein said support has a layer of water resistant material lining the inner surface of said support.

6. The method for the relief or treatment of painful or tender breasts in a lactating woman, which method comprises the steps of: heating or cooling said breast cover as defined in claim 1, mounting said breast cover to said support and attaching said support to a woman's upper body such that said breast cover at least partially contacts one or both breasts so as to heat or cool said one or both breasts.

* * * * *